(12) United States Patent
Nagasaki et al.

(10) Patent No.: US 8,246,992 B2
(45) Date of Patent: Aug. 21, 2012

(54) β-1,3-GLUCAN-DERIVED POLYALDEHYDE/POLYAMINE HYDROGEL

(75) Inventors: Takeshi Nagasaki, Osaka (JP); Tatsuro Hayashi, Nara (JP); Kenji Oohata, Osaka (JP); Kenichi Ishibashi, Osaka (JP); Toshio Suzuki, Osaka (JP); Yoshiro Furukawa, Osaka (JP)

(73) Assignees: Osaka City University, Osaka (JP); Daiso Co., Ltd., Osaka (JP)

( * ) Notice: Subject to any disclaimer, the term of this patent is extended or adjusted under 35 U.S.C. 154(b) by 0 days.

(21) Appl. No.: 12/734,425

(22) PCT Filed: Nov. 4, 2008

(86) PCT No.: PCT/JP2008/070052
§ 371 (c)(1),
(2), (4) Date: Aug. 27, 2010

(87) PCT Pub. No.: WO2009/057802
PCT Pub. Date: May 7, 2009

(65) Prior Publication Data
US 2010/0316719 A1    Dec. 16, 2010

(30) Foreign Application Priority Data

Nov. 1, 2007 (JP) .................. 2007-285087
Jul. 10, 2008 (JP) .................. 2008-180178

(51) Int. Cl.
*A61K 9/14* (2006.01)
(52) U.S. Cl. .................................... 424/486
(58) Field of Classification Search .................. None
See application file for complete search history.

(56) References Cited

U.S. PATENT DOCUMENTS

| | | | |
|---|---|---|---|
| 6,107,358 A * | 8/2000 | Harada et al. | 521/133 |
| 6,406,897 B1 | 6/2002 | Kim et al. | |
| 6,514,522 B2 * | 2/2003 | Domb | 424/443 |
| 6,642,363 B1 * | 11/2003 | Mooney et al. | 536/3 |
| 6,790,840 B1 * | 9/2004 | Lee et al. | 514/54 |
| 7,223,571 B2 * | 5/2007 | DeAngelis et al. | 435/97 |
| 2005/0136516 A1 * | 6/2005 | Ho et al. | 435/72 |
| 2006/0019378 A1 | 1/2006 | Nagasaki et al. | |
| 2006/0134185 A1 * | 6/2006 | Odermatt et al. | 424/443 |
| 2006/0239958 A1 | 10/2006 | Taguchi et al. | |
| 2006/0246585 A1 | 11/2006 | Nagasaki et al. | |
| 2008/0019918 A1 * | 1/2008 | Aoki et al. | 424/9.3 |

FOREIGN PATENT DOCUMENTS

| | | |
|---|---|---|
| EP | 1806367 A2 * | 7/2007 |
| EP | 1849486 A1 * | 10/2007 |
| JP | 60-152501 | 8/1985 |
| JP | 07-300563 | 11/1995 |
| JP | 2000-273182 | 10/2000 |
| JP | 2003-119290 | 4/2003 |
| JP | 2003-171462 | 6/2003 |
| JP | 2003-171463 | 6/2003 |
| JP | 2003-171464 | 6/2003 |
| JP | 2003-176353 | 6/2003 |
| JP | 3502879 | 12/2003 |
| JP | 2004-261222 | 9/2004 |
| JP | 2004-321177 | 11/2004 |
| JP | 2005-21454 | 1/2005 |
| JP | 2006-304644 | 11/2006 |
| JP | 2007-20444 | 2/2007 |
| JP | 2008-93230 | 4/2008 |
| WO | 2006/080523 | 8/2006 |

OTHER PUBLICATIONS

Tony Azzam, Hagit Eliyahu, Libi Shapira, Michel Linial, Yechezkel Barenholz, and Abraham J. Domb. Polysaccharide—Oligoamine Based Conjugates for Gene Delivery. J. Med. Chem., 2002, 45 (9), pp. 1817-1824.*

Tony Azzam, Hagit Eliyahu, Libi Shapira, Michal Linial, Yechezkel Barenholz, and Abraham J. Domb. Polysaccharide—Oligoamine Based Conjugates for Gene Delivery. J. Med. Chem., 2002, 45 (9), pp. 1817-1824.*

Tin W. Wong. Chitosan and Its Use in Design of Insulin Delivery System. Recent Patents on Drug Delivery & Formulation, vol. 3, No. 1, Jan. 2009 , pp. 8-25(18). Publisher: Bentham Science Publishers.*

D. Guilmet et al., "Use of Biological Glue in Acute Aortic Dissection: Preliminary Clinical Results with a New Surgical Technique", The Journal of Thoracic and Cardiovascular Surgery, vol. 77, No. 4, pp. 516-521, Apr. 1979.

T. Nagasaki et al., "Long-Term Expression with a Cationic Polymer Derived from a Natural Polysaccharide: Schizophyllan", Bioconjugate Chemistry, vol. 15, No. 2, pp. 249-259, 2004.

Kawamura M et al., Journal of Japan Surgery Society, vol. 103, p. 261, 2002 (concise explanation found in instant specification, paragraph [0002], p. 1, lines 14-22).

Gen S et al., "Biodegradable Soft Tissue Adhesive of the 2 Liquid Reaction Type", Journal of Japan Dental Materials, vol. 25, No. 5, p. 401, 2006 (concise explanation found in instant specification, paragraph [0004], p. 2, line 9 to p. 3, line 1).

Taguchi T, Engineering Materials, vol. 55, No. 3, pp. 41-45, 2007 (concise explanation found in instant specification, paragraph [0005], p. 3, lines 2-15).

* cited by examiner

*Primary Examiner* — Robert A Wax
*Assistant Examiner* — Olga V Tcherkasskaya
(74) *Attorney, Agent, or Firm* — Wenderoth, Lind & Ponack, L.L.P.

(57) ABSTRACT

The present invention provides a combination product which comprises:

(1) a polyaldehyde obtained by introducing an aldehyde group into a branched glucose in a β-1,3-glucan, and (2) a polyamine obtained by increasing the molecular weight of a poly-L-lysine.

The combination product according to the present invention is useful as a material for a tissue adhesive hydrogel which can be used as a hemostatic agent or the like which exhibits low risks for viral infections and the like, high biodegradability and biocompatibility, excellent safety, a good adhesion rate and a good adhesion strength.

11 Claims, 4 Drawing Sheets

| | | |
|---|---|---|
| EG-PLL | + | + |
| 2.0-CHO | + | − |
| 0-CHO-β-1,3-glucan | − | + |

β-1,3-GLUCAN-DERIVED POLYALDEHYDE/POLYAMINE HYDROGEL

TECHNICAL FIELD

The present invention relates to a material and a method for producing a tissue adhesive hydrogel exhibiting biocompatibility and biodegradability and having excellent gelation kinetics and strength which are the properties required for a hemostatic agent for surgeries such as cerebral and cardiac surgery and the like.

BACKGROUND ART

Recent characteristics of surgeries include rapidity and greater sophistication. Therefore, limitations of traditional astriction and sutural hemostasis are worthy of attention. A fibrin adhesive, which is a currently commercially available hemostatic agent and a tissue adhesive, has problems involving a high risk of viral infection and a weak adhesive strength (Non-Patent literature 1).

In addition, a polyamine-aldehyde system, which is clinically used in addition to the fibrin adhesive, and which is obtained by hardening gelatin by means of adding cross-linking agents such as formaldehyde, glutaraldehyde or the like, has been found to carry the risk of causing residual disabilities such as vessel-clogging and significant neurological problems and tissue damage due to the presence of low-molecular-weight aldehyde compounds and, therefore, it is unsuitable for use (Non-Patent literature 2).

In order to overcome these problems, a number of studies have been carried out. For example, an adhesive agent derived from the cross-linked Schiff base formation between dextran which is obtained from food additives and ε-poly-L-lysine (hereinafter, called ε-PLL) has been studied, but its gel strength is lower than that of fibrin adhesive which is a commercially available hemostatic agent and this insufficient strength as a hemostatic agent is a problem. Regarding the cause of this problem, it is thought that the periodate oxidation conducted on polysaccharides in order to make them aldehyde causes the ring-opening of main chain glucose of dextran. In the process of this periodate oxidation, aldehyde groups are introduced into the main chain, but, at the same time, the main chain scission occurs and then the molecular weight of dextran decreases, which may bring about a decrease in the gel strength (Non-Patent literature 3).

As an adhesive agent exhibiting excellent strength, a tissue adhesive which comprises active ester derivatives of citric acid and proteins such as collagen as adhesive components has been studied. However, the active ester compound is chemically unstable and it is impossible to store the compound for a long time in the form of an aqueous solution. Therefore, the active ester compound is required to be dissolved immediately before use in solvent which carries the risk of bringing about adverse effects on living organisms. Further, there might be some problems when a medical doctor uses it in an emergency during surgical procedures (Patent literature 1 and Non-Patent literature 4).

[Patent literature 1] JP-A-2004-261222
[Non-Patent literature 1] Masafumi KAWAMURA, Yoshinari KIMURA, Ikuo KAMIYAMA, Takahiko KOYAMA, Taichiro GOTO, Manabu YAMAMOTO, Yoshimasa INOUE, Takashi OTSUKA, Hayanori HORIGUCHI, Tokuko YAMAUCHI, Makoto FUJISAWA, Masazumi WATANABE, Hirohisa HIRINOUCHI, Koichi KOBAYASHI, Journal of Japan Surgery Society, 103, 261 (2002)
[Non-Patent literature 2] D. Guilmet, J. Bachet, B. Goudot, C. Laurian, F. Gigou, O. Bical, M. Barbagelatta, J. Thorac. Cardiovasc. Surg., 77, 516(1979)
[Non-Patent literature 3] Shokyu GEN, Naoki NAKAJIMA, Hajime SUGAI, Sadami TSUTSUMI, J J Dent Mater 25, 401 (2006)
[Non-Patent literature 4] Tetsushi TAGUCHI, Engineering Materials, 55, 41 (2007)

DISCLOSURE OF INVENTION

Problems Intended to be Solved by the Invention

One object of the present invention is to develop materials for tissue adhesive hydrogel and techniques for producing the hydrogel which can be used as a hemostatic agent and the like suitable for use in current surgical procedures, i.e. that carries a low risk of viral infections and the like, has biodegradability and biocompatibility, and exhibits excellent safety as well as good adhesive rate and strength.

Means for Solving the Problems

First of all, it is effective for ensuring safety to utilize natural polymer molecules having biodegradability and biocompatibility which had previously been used as food additives or pharmaceutical agents. Further, in order to improve the tissue adhesive effect caused by the formation of hydrogel, use of materials which can form hydrogel with high gel strength is required.

Considering the above problems, the present inventors have conducted intensive studies and found that certain types of polyamine and polyaldehyde are effectively used as materials for producing such hydrogel.

As regards polyamine, one obtained by increasing the molecular weight of ε-PLL (poly-L-lysine) is used. ε-PLL (represented by the following general formula (I)) has been approved for use in food additives or quasi-drugs and is recognized as excellent in terms of safety. On the other hand, as regards polyaldehyde, one obtained by introducing an aldehyde group selectively into a branched glucose in a β-1,3-glucan is used. β-1,3-glucan (represented by, for example, the following formula (II)) derived from microorganisms such as fungi and yeasts has been confirmed to be safe as pharmaceuticals or supplements and has branched glucoses. The combination product of the polyamine and the polyaldehyde was found to be able to form a hydrogel having high biocompatibility, excellent safety, adhesive rate and adhesive strength, and then the present invention was completed.

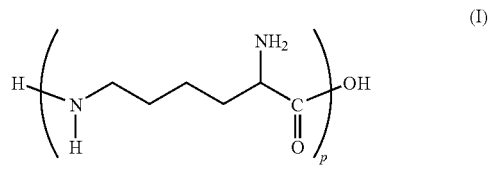
(I)

In the present invention, "ε-PLL" which is raw material for producing the polyamine, refers to the compound represented by the general formula (I), wherein p is from 10 to 50 and preferably p is from 20 to 40 and more preferably p is from 25 to 35.

In the present invention, "polyamine obtained by increasing the molecular weight of a poly-L-lysine" includes both a product obtained by condensing ε-PLL represented by the general formula (I) such that the molecular weight of the product is from 4,000 to 200,000 and a product obtained by increasing the molecular weight of ε-PLL represented by the general formula (I) by cross-linking ε-PLL with a cross-linking agent such that the molecular weight of the product is from 4,000 to 200,000. Preferably, the molecular weight of "polyamine obtained by increasing the molecular weight of a poly-L-lysine" is from 10,000 to 150,000 and more preferably from 20,000 to 100,000. The amount of primary amino group in the molecule which can form the Schiff base is about 10-50% of the amount of N which is measured by elemental analysis given that the molar ratio of cross-linking agent, ε-PLL (I) relative to NH2 group is 0.22. Preferably, the amount of primary amino group in the molecule which can form the Schiff base is about 25-35%, more preferably 28% of the amount of N which is measured by elemental analysis.

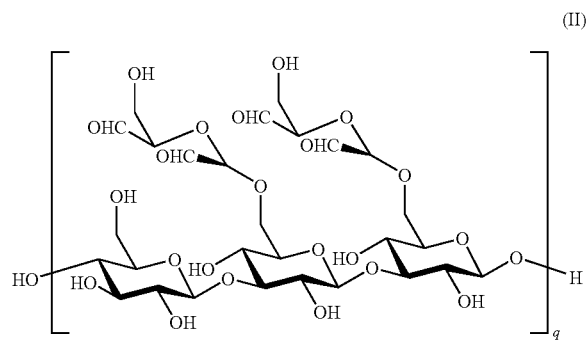

(II)

In the present invention, "polyaldehyde obtained by introducing an aldehyde group into a branched glucose in a β-1,3-glucan" refers to a polysaccharide in which β-glucoses are linked by β (1-3) binding (β-1,3-glucan) that has branched glucoses which are linked by β(1-6) binding, wherein a part or all of the branched glucoses' 2,3-diol and/or 3,4-diol is oxidized such that aldehyde groups are introduced into the polysaccharide. The structure of the polyaldehyde of the present invention is not limited to that represented by the general formula (II), but examples of the polyaldehyde include those represented by the general formula (II), wherein q is from 12 to 362, and preferably q is from 60 to 240. The molecular weight of the polyaldehyde of the present invention is from 9,000 to 270,000, and preferably from 45,000 to 180,000. In addition, the position and the ratio of branched glucose in β-1,3-glucan are not particularly limited.

Regarding the amount of aldehyde group in the polyaldehyde molecule, from 10 to 99% of repeating units constituting the general formula (II) are oxidized such that aldehyde groups are introduced, preferably from 10 to 95%, and more preferably from 20 to 95% of repeating units are oxidized such that aldehyde groups are introduced. In addition, the ratio of branched glucose in β-1,3-glucan means the proportion of the number of branched glucoses relative to the number of main chain glucoses and represented by the following equation:

The ratio of branched glucose in β-1,3-glucan=the number of β-1,6 binding/the total number of β-1,3 binding+β-1,6 binding.

Accordingly, the present invention provides a combination product comprising:
(1) a polyaldehyde obtained by introducing an aldehyde group into a branched glucose in a β-1,3-glucan, and
(2) a polyamine obtained by increasing the molecular weight of a poly-L-lysine.

Preferably, of the polyaldehyde obtained by introducing an aldehyde group into a branched glucose in a β-1,3-glucan and the polyamine obtained by increasing the molecular weight of a poly-L-lysine, at least one is in the form of an aqueous solution and more preferably, both are in the form of aqueous solutions.

In addition, it is preferable that the polyaldehyde be obtained by introducing an aldehyde group into a branched glucose in a β-1,3-glucan by means of periodate oxidation of the branched glucose. The periodate oxidation of the branched glucose in β-1,3-glucan is preferably carried out under alkaline conditions. Preferably, the ratio of branched glucose in β-1,3-glucan is equal to or greater than 60%.

On the other hand, the polyamine obtained by increasing the molecular weight of a poly-L-lysine is preferably obtained by bridging ε-poly-L-lysine by means of a cross-linking agent, and the preferable cross-linking agent is diglycidylether. Further, the molecular weight of the polyamine obtained by increasing the molecular weight of a poly-L-lysine determined by SDS-PAGE is preferably equal to or greater than 10,000.

The present invention further provides a tissue-adhesive hydrogel produced by using the combination product as described above, which comprises:
(1) a polyaldehyde obtained by introducing an aldehyde group into a branched glucose in a β-1,3-glucan, and
(2) a polyamine obtained by increasing the molecular weight of a poly-L-lysine.

Furthermore, the present invention provides a method for producing the tissue-adhesive hydrogel as described above, which comprises mixing:
(1) a polyaldehyde obtained by introducing an aldehyde group into a branched glucose in a β-1,3-glucan, and
(2) a polyamine obtained by increasing the molecular weight of a poly-L-lysine.

The present invention further provides a hemostatic composition comprising a hydrogel obtained by mixing:
(1) a polyaldehyde obtained by introducing an aldehyde group into a branched glucose in a β-1,3-glucan, and
(2) a polyamine obtained by increasing the molecular weight of a poly-L-lysine.

The present invention also provides a hemostatic composition comprising:
(1) a polyaldehyde obtained by introducing an aldehyde group into a branched glucose in a β-1,3-glucan,
(2) a polyamine obtained by increasing the molecular weight of a poly-L-lysine, and
(3) a hemostatic sponge or sheet.

Preferably, the hemostatic sponge or sheet is a collagen sponge.

The tissue adhesive hydrogel obtained by using the combination product of the present invention which comprises: (1) a polyaldehyde obtained by introducing an aldehyde group into a branched glucose in a β-1,3-glucan, and (2) a polyamine obtained by increasing the molecular weight of a poly-L-lysine is suitably used as a hemostatic agent for brain, heart, liver and the like, as a vascular blockage agent, as a lung-sealant, as a sealant for aneurysm or the like.

Further, the tissue adhesive hydrogel obtained by using the combination product of the present invention, which comprises (1) a polyaldehyde obtained by introducing an aldehyde group into a branched glucose in a β-1,3-glucan, and (2) a polyamine obtained by increasing the molecular weight of a poly-L-lysine, is suitably used as a living tissue adhesive which adheres soft tissue to soft tissue such as in a blood vessel anastomosis site, soft tissue to hard tissue such as living tendon and bone or parodontal tissue and tooth or the like as well as hard tissue to hard tissue such as bone and bone or tooth and tooth or the like.

Effect Exhibited by the Invention

The tissue adhesive hydrogel obtained by using the combination product of the present invention exhibits good gelation kinetics and gel strength and can covalently bind to amine components in living tissues and, therefore, is highly tissue-adhesive. In addition, both components of the combination product of the present invention are derived from natural products and are biodegradable/bioabsorbable. Both components not only exhibit high biocompatibility but also have high molecular weight and, therefore, their permeability into tissues is low. Accordingly, the tissue adhesive hydrogel obtained by using the combination product of the present invention has low tissue toxicity and can be safely and suitably used as a biodegradable/bioabsorbable hemostatic agent.

BEST MODE OF USE FOR THE INVENTION

The combination product of the present invention is a combination of a polyaldehyde derived from a polysaccharide, which is a natural biodegradable high molecular-weight product, and a biodegradable polyamine.

First of all, the first component of the combination product of the present invention, which is a polyaldehyde obtained by introducing an aldehyde group into a branched glucose in a β-1,3-glucan (1), is explained.

The polyaldehyde obtained by introducing an aldehyde group into a branched glucose in a β-1,3-glucan (1) (hereinafter, referred to simply as polyaldehyde (1)) which is used for the combination product of the present invention is a polyaldehyde obtained by introducing an aldehyde group into 10-95%, preferably 25-95%, of all branched glucoses existing in β-1,3-glucan which is approved for the use in supplements or foods.

In the polyaldehyde (1) used in the present invention, the ratio of branched glucose in β-1,3-glucan is preferably from 5 to 80%, more preferably equal to or greater than 60% and the most preferably, equal to or greater than 65%.

In the aldehydation to make a polyaldehyde, oxidation agents such as periodate and lead tetraacetate can be used. A preferable oxidation agent is periodate. In the reaction which employs periodate, a homogeneous reaction which employs water as solvent, a two-phase reaction system which employs phase-transfer catalyst and a heterogeneous reaction which employs silica gel are effectively used. Preferably, aldehyde groups are introduced via the periodate oxidation which employs, as a solvent, a mixed solvent which comprises water and a polar solvent which can be compatible with water at any ratio (DMSO, DMF, NMP, THF, methanol and ethanol), preferably water alone, and as a reagent, periodate (sodium periodate, potassium periodate), preferably sodium periodate. The amount of the periodate is from 0.1 to 20 eq., preferably from 1 to 15 eq., and more preferably from 2 to 10 eq. based on the amount of branched glucose. The reaction temperature of the periodate oxidation is from 4 to 50° C., preferably from 4 to 25° C., more preferably 4° C. and the reaction time is from 2 to 72 hours, preferably from 12 to 64 hours, and more preferably from 24 to 48 hours. The reaction pressure of the periodate oxidation is from 1 to 5 atmospheres, preferably from 1 to 2 atmospheres, and more preferably 1 atmosphere.

The periodate oxidation is preferably conducted under alkaline conditions. Examples of alkaline conditions include preferably pH 11 to 14, more preferably pH 12 to 13 and the most preferably pH 13. Examples of reagents which make the alkaline conditions are not limited but include sodium hydroxide.

Figure 1:
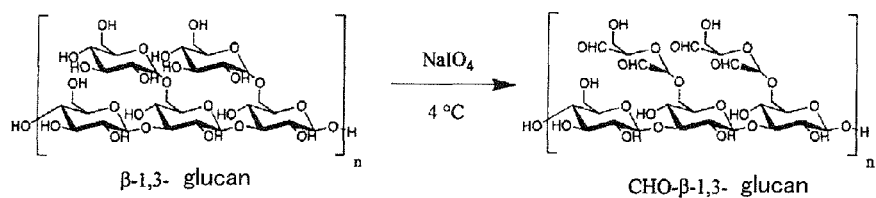
FIG. 1 is a schematic representation of the synthesis of the polyaldehyde used in the present invention.

Since β-1,3-glucan does not have 1,2-diol in its main chain, when it is subjected to the periodate oxidation, aldehyde groups are selectively introduced into branched glucoses as shown in FIG. 1 and the structure of the main chain is not affected. Therefore, by adjusting the molar ratio of periodate to the molar amount of branched glucose to 0.1-20 equivalents, one can easily control the introduction of aldehyde groups such that a product into which aldehyde groups are introduced at a ratio of 10-99% of repeating units constituting the general formula (II) is produced. In addition, by the periodate oxidation, the possibility of the main chain scission due to the change in the main chain structure will be decreased and, therefore, a gel with higher strength can be formed (T. Nagasaki, M. Hojo, A. Uno, T. Satoh, K. Koumoto, M. Mizu, K. Sakurai, and S. Shinkai, Bioconjugate Chem., 15, 249-259 (2004)).

Secondly, the second component of the combination product of the present invention, which is a polyamine obtained by increasing the molecular weight of a poly-L-lysine (2), is explained.

The polyamine obtained by increasing the molecular weight of a poly-L-lysine (2) used for the combination product of the present invention (hereinafter, referred to simply as polyamine (2)) is a polyamine obtained by increasing the molecular weight of ε-PLL, which is approved for the use as food additives or quasi-drugs, by various methods. By increasing the molecular weight of ε-PLL, ε-PLL alone is known to turn into a gel and to exhibit the effect of preventing bleeding from a location of hemorrhage if it has a great viscosity (JP-A-2003-171463 and JP-A-2003-176353).

The polyamine (2) used for the combination product of the present invention is obtained by reacting and linking ε-PLL represented by the general formula (I) with one another, if desired by using a cross-linking agent, such that the molecular weight of the polyamine will be increased. Examples of methods for increasing the molecular weight of ε-PLL include: (1) subjecting ε-PLLs to polycondensation, (2) subjecting ε-PLLs to the radiation processing such that ε-PLLs are linked to one another, and (3) subjecting ε-PLL molecules to the cross-linking reaction which employs a cross-linking agent such that ε-PLL molecules be cross-linked via the cross-linking agent. In the "polyamine obtained by increasing the molecular weight of a poly-L-lysine (2)", it is not necessary that all ε-PLL molecules be linked together. Rather, as a result of the processing described above, the "polyamine obtained by increasing the molecular weight of a poly-L-lysine (2)" may be one which can be confirmed, for example by electrophoresis, as including high-molecular-weight products which are formed by a method whereby at least a portion of ε-PLL molecules are linked together and the other portions of ε-PLL molecules may remain as unreacted portions. Preferably, the molecular weight of the polyamine is increased such that molecules whose molecular weight is equal to or lower than two folds of the average molecular weight of ε-PLL before being subjected to the molecular-weight increasing processing is observed either hardly or not at all by means of electrophoresis. More preferably, the molecular-weight increasing processing is conducted such that molecules whose molecular weight is equal to or greater than ten folds of the average molecular weight of ε-PLL before being subjected to the molecular-weight increasing processing are apparently observed by means of electrophoresis.

The polycondensation as explained in the above option (1) is preferably conducted by heating ε-PLL to 150-200° C. for 20-90 minutes in vacuo or under the atmosphere of inert gas.

The radiation processing as explained in the above option (2) can be carried out, for example, by a known method which is disclosed in Japanese Patent No. 3502879. The radiation processing can be carried out by irradiating an aqueous solution of ε-PLL with radioactive rays or neutron rays, preferably γ-rays. When γ-rays are used for irradiation, the irradiance level is usually, but not limited to, about 45-250 kGy.

Figure 2:
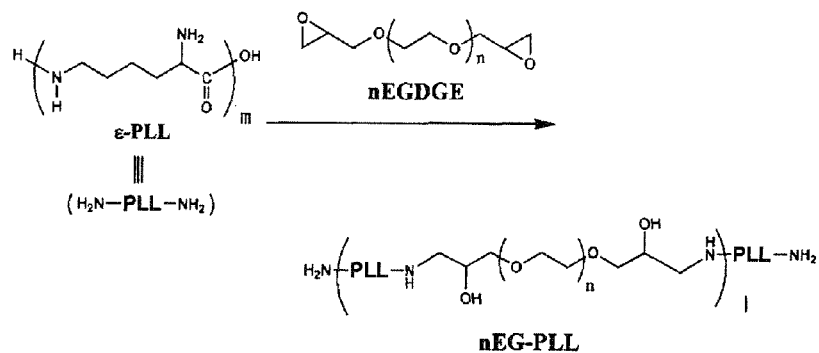
FIG. 2 is a synthetic schematic of the polyamine used in the present invention which is high-molecular-weight ε-PLL (nEG-PLL) from ε-PLL.

The cross-linking reaction which employs a cross-linking agent as explained in the above option (3) can be carried out, for example, by a known method which is disclosed in JP-A-2003-171464. The cross-linking agent is not particularly limited as long as it contains two or more functional groups which can react with an amino group of εPLL. Examples of the functional groups of the cross-linking agent include an aldehyde group, a carboxylic acid chloride, a carboxylic acid anhydride, and an active ester of carboxylic acid (N-hydroxysuccinimide ester, p-nitrophenyl ester, pentachlorophenyl ester) structure. For example, as illustrated in FIG. 2, epoxy compounds which have two or more glycidyl groups such as ethylene glycol diglycidylether, dipropylene glycol diglycidylether and the like are preferably used as the cross-linking agent. Preferably, 0.1-10 wt % of εPLL (30-mer) is dissolved in a solvent and is subjected to the cross-linking reaction in the aqueous solution which employs 0.05-0.30 molar amount of an epoxy compound based on the molar amount of εPLL (30-mer) at a temperature of 25-100° C. Preferably, said cross-linking agent is diglycidylether. Examples of preferable diglycidylether include nEGDGE (n-ethylene glycol diglycidylether) shown in FIG. 2, wherein n is from 1 to 50.

The origin of ε-PLL represented by the general formula (I) is not limited. ε-PLL may be obtained by any known method. ε-PLL may be obtained from lysine by means of chemical synthesis. However, the chemical synthesis of ε-PLL requires high skill-level and the chemically synthesized ε-PLL is expensive. Therefore, it is preferable to obtain ε-PLL by the method disclosed in Japanese Patent No. 1245361 which employs *Streptomyces albulus* subsp. *lysinopolymerus*. The method comprises culturing *Streptomyces albulus* subsp. *lysinopolymerus* in a medium which contains, for example, 5 weight % of glucose, 0.5 weight % of yeast extract, 1 weight % of ammonium sulfate, 0.08 weight % of dibasic potassium phosphate, 0.136 weight % of potassium dihydrogen phosphate, 0.05 weight % of magnesium sulfate heptahydrate, 0.004 weight % of zinc sulfate heptahydrate and 0.03 weight % of iron sulfate heptahydrate and whose pH is adjusted to pH 6.8, isolating and collecting ε-PLL from the resulting culture media. Alternatively, ε-PLL may be obtained by the method disclosed in JP-A-2003-171462, which employs microbial fermentation.

The molecular weight, which may be observed by SDS-PAGE, of the polyamine (2) obtained by increasing the molecular weight of poly-L-lysine optionally by means of a cross-linking agent used for the present invention is preferably confirmed to be from about 4,000 to about 500,000 in terms of gel-forming ability, cytotoxicity and degradability. The molecular weight of the polyamine (2) which may be observed by SDS-PAGE is preferably 10,000 to 400,000, for example, 10,000 to 250,000 and more preferably from about 20,000 to about 150,000.

In the present invention, the polyamine (2) may be fractionated based on the molecular weights of their components, if desired. By conducting the fractionation, polyamine components having a desired range of molecular weights can be collected. Methods for fractionating the polyamine components based on their molecular weights are not particularly limited and include, as examples, gel filtration chromatography, ultrafiltration, ion-exchange chromatography, and preparative SDS-PAGE.

The combination product of the present invention is usually a two-component system which contains polyaldehyde (1) and polyamine (2) separately. Preferably, the combination product of the present invention is a two-component system which contains an aqueous solution containing polyaldehyde (1) and another aqueous solution containing polyamine (2) separately. In other words, at least one of polyaldehyde (1) and polyamine (2) is preferably in the form of an aqueous solution and more preferably, both polyaldehyde (1) and polyamine (2) are in the forms of aqueous solutions. Each of polyaldehyde (1) and polyamine (2) can be stably stored in an aqueous solution. By providing both polyaldehyde (1) and polyamine (2) as aqueous solutions, a gel can be rapidly formed upon mixing the aqueous solutions containing each of the two components.

The components (1) and (2) turn into a gel not only in an aqueous solution but also in substrates in the presence of water such as hemostatic sponges and sheets which are used as hemostatic devices. Examples of hemostatic sponges or sheets include collagen sheets, chitosan sheets, gelatin sheets and the like (these materials may be in forms other than sheets, such as in the form of sponge and the like).

In addition, the combination product of the present invention may be one obtained by mixing, in addition to components (1) and (2), agents such as water-soluble anti-inflammatory drugs, antibacterial agents, angiogenic drugs and the like.

Examples of solvents which are used to convert these two components into aqueous solutions include distilled water, an aqueous solution which contains a metal ion that interacts with biodegradable polymers via electrostatic interaction or chelating effect and a buffered solution and the like. These solvents are not organic solvents and, therefore, do not exhibit high toxicity to living tissues. The use of these solvents makes it possible to prevent living tissues surrounding the site to which the tissue adhesive hydrogel of the present invention is attached from necrotizing due to the changes in osmotic pressure and in pH. A buffered solution is preferably used because it can control pH of the solution between pH 6 and 8, which may result in the control of gelation kinetics.

The polyaldehyde (1) and the polyamine (2) can be provided in the form of lyophilized powder or the like as well as in the form of aqueous solutions. When both components are provided in a form other than that of an aqueous solution, these components are mixed with solvents such as DMSO, DMF, NMP, THF, methanol, ethanol and the like such that a gel is formed.

Examples of buffered solutions include those containing one or more components which are selected from hydrochloride, sulfate, nitrate, phosphate, carbonate and borate. Examples of buffered solutions further include sodium hydrogen carbonate buffered solution, borate buffered solution, and phosphate buffered solution and the like. The concentration range of inorganic salts which are used for preparing buffered solutions is preferably from 0.01 M to 10.0 M.

When the polyaldehyde (1) and/or the polyamine (2) is provided as an aqueous solution, the concentration of (1) is preferably from 2 to 20 wt % and that of (2) is preferably from 5 to 15 wt % based on the amount of solvents such as distillated water, an aqueous solution containing a metal ion, a buffered solution and the like. Methods for preparing a concentrated solution containing (1) or (2) include a vacuum concentration method and a freeze-drying method. The concentrations of (1) and (2) in the gel formed by mixing the combination product of the present invention are both preferably from 2 to 10 wt %. The weight ratio of (1):(2) in the gel is from 1:1 to 1:10 and preferably from 1:1 to 1:5.

The present invention also provides a tissue adhesive hydrogel which is formed by using the polyaldehyde (1) and the polyamine (2) as well as a method for producing tissue adhesive hydrogel which comprises the step of mixing polyaldehyde (1) and polyamine (2).

In the combination product of the present invention, the reaction between the polyaldehyde (1) and the polyamine (2) occurs. In more detail, aldehyde groups in the polyaldehyde and amino groups in the polyamine form the Schiff base binding such that a gel is formed.

According to the present invention, the rapid gelation occurs when components (1) and (2) are brought into contact in the presence of water, for example, in an aqueous solution or in a hemostatic sponge or sheet. Tissue adhesive hydrogel thus formed can be used as an adhesive for warm-blooded animal tissues, more specifically as a hemostatic agent used in surgical procedures or in the treatment of wounds. When the hydrogel is applied to tissues, a portion of aldehyde groups contained in the hydrogel reacts with amino groups or the like which are present in tissue proteins or lipid molecules which constitute biomembranes and, therefore, the hydrogel also binds to tissues. Because of this kind of reaction, not only is the hemostatic effect exhibited in the treatment improved, but also the sustained hemostatic effect is exhibited because the hydrogel does not move from the treatment site after the hemostatic treatment.

In terms of the above effect, it is preferable that not all aldehyde groups be subjected to the reaction for forming the gel and that some aldehyde groups remain unreacted.

The tissue adhesive hydrogel comprising the polyaldehyde obtained by introducing an aldehyde group selectively into a branched glucose in a β-1,3-glucan and the polyamine obtained by increasing the molecular weight of ε-PLL exhibits high biocompatibility and is excellent in terms of safety, adhesion rate and strength and, therefore, is useful as a hemostatic agent.

The present invention is further explained by the following Examples but the present invention should not be limited by the Examples.

EXAMPLES

The Preparation of the Polyaldehyde from β-1,3-Glucan

Aldehyde groups were introduced into branched glucoses in β-1,3-glucan according to the synthesis scheme shown in FIG. 1, Specifically, 100 mg of β-1,3-glucan (DAISO, AQUA β powder) having branched glucoses was dissolved in 5 ml of water by stirring at room temperature. To this solution, various molar equivalents of meta-sodium periodate in relation to the mol concentration of the branched glucoses in β-1,3-glucan were added as shown in Table 1 and the solution was subjected to the reaction at 4° C. for 24 hours. To the solution, 10 ml of water was added and small molecules contained in the solution were removed by dialysis (Spectra/Por®7, MWCO 3,500). After the dialysis, the solution was concentrated by means of an evaporator to give an aqueous solution of polyaldehyde derivative. A portion of the solution was lyophilized in order to determine the weight concentration of the solution. After the concentration, the solution was stored overnight at room temperature. As a result, all aldehyde derivatives which were synthesized under neutral conditions jellified and exhibited high viscosity though they exhibited some flowability. On the other hand, aldehyde derivatives which were synthesized under alkaline conditions were in the form of liquid which exhibited appropriate viscosity and were suitable for further treatments.

The Preparation of the Polyaldehyde from β-1,3-Glucan Under Alkaline Conditions 300 mg of β-1,3-glucan (DAISO, AQUA β powder) having branched glucoses was dissolved in 20 ml of 125 mM aqueous solution of NaOH by means of stirring with a magnetic stirrer at room temperature. To this solution, 10 equal parts of meta-sodium periodate based on the mol concentration of branched glucoses was added and the solution was subjected to the reaction at 4° C. for 24-72 hours. Then, in order to remove insoluble materials which crystallized, the solution was filtrated with a KIRIYAMA funnel (No. 3, 40 φm/m), washed (10 ml×three times) and subjected to dialysis (Spectra/Por™7, MWCO 3,500) such that low molecular weight compounds were removed. After the dialysis, the solution was concentrated by means of an evaporator to give polyaldehyde derivatives. A portion of the solution was lyophilized in order to determine the weight concentration of the solution. After the concentration, all polyaldehyde derivatives existed as pale yellow transparent solutions. Since these solutions were prepared by a method different from the above-described method, these solutions were named Alkali-10-CHO.

TABLE 1

Reaction conditions of polyaldehyde synthesis

| | β-1,3-glucan [mg] | Side chain glucose [μmol] | NaIO₄ [mg] | NaIO₄ [μmol] | Molar ratio [eq] | Product Name | Introduction ratio of CHO [%] | Amount [mg] | Yield [%] |
|---|---|---|---|---|---|---|---|---|---|
| 1 | 100 | 241 | 25.8 | 120.5 | 0.5 | 0.5-CHO | 36 | 51.8 | 56 |
| 2 | 100 | 241 | 51.6 | 241 | 1.0 | 1.0-CHO | 59 | 50.4 | 54 |
| 3 | 100 | 241 | 103 | 482 | 2.0 | 2.0-CHO | 84 | 32.8 | 36 |
| 4 | 100 | 241 | 258 | 1205 | 5.0 | 5.0-CHO | 94 | 41.2 | 45 |
| 5 | 100 | 241 | 516 | 2410 | 10 | 10-CHO | 94 | 39.2 | 41 |
| 6* | 300 | 723 | 1548 | 7230 | 10 | Alkali-10-CHO | 63 | 147 | 53 |

*125 mM NaOH aqueous solution was used as a reaction solution and the reaction time was 24 hours.

Figure 3:
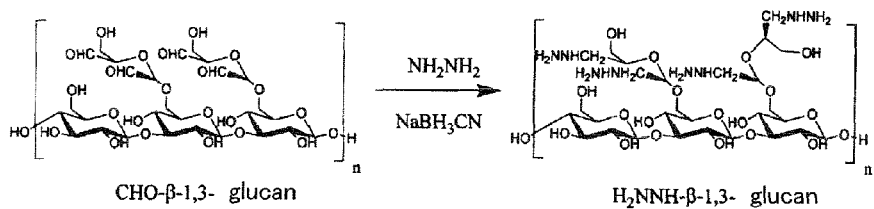
FIG. 3 is a synthetic schematic of a hydrazine compound which is used for calculating the ratio of the introduction of aldehyde into the side chain of an exemplary polyaldehyde derived from β-1,3-glucan used in the present invention.
Figure 4:
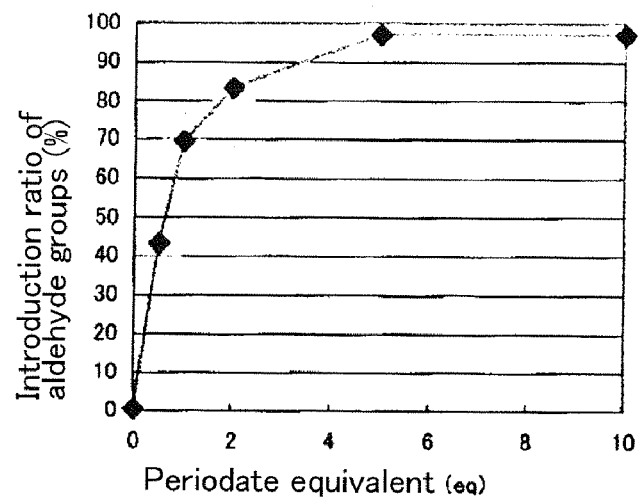
FIG. 4 is a graph showing the ratio of the introduction of aldehyde into the polyaldehyde derived from β-1,3-glucan based on the periodate equivalent.

Calculation of the Introduction Ratio of Aldehyde Groups Into Branched Glucose Residues by Using Hydrazine The introduction ratios of aldehyde groups into polyaldehyde derivatives were determined. At first, hydrazine and aldehyde groups were reacted such that Schiff bases were formed according to the scheme illustrated in FIG. 3. The resulting product was subjected to the reduction by $NaBH_3CN$ such that hydrazinated β-1,3-glucan ($H_2NNH$-β-1,3-glucan) was synthesized. A portion of the hydrazinated β-1,3-glucan solution was lyophilized and subjected to elemental analysis. The result of the elemental analysis which shows N % was used for calculating the introduction ratio of aldehyde groups. The result is shown in FIG. 4. When the periodate equivalent based on the number of branched glucoses upon the oxidation reaction was increased, the introduction ratio of aldehyde groups was elevated and when the periodate equivalent was 5 eq, branched glucoses were aldehydated approximately quantitatively. Further, under alkaline conditions, the introduction ratio of aldehyde groups was decreased. It was shown that the reactivity under alkaline conditions was low. However, even under alkaline conditions, when the reaction time was prolonged to 72 hours, the introduction ratio of aldehyde groups was increased to 83% and it was not significantly different from the introduction ratio observed under neutral conditions.

Preparation of Polyamine which Comprises Increasing the Molecular-Weight of ε-PLL According to the synthesis scheme shown in FIG. 2, the molecular weight of E-PLL was made to increase. 0.5 g of ε-PLL (Mol wt. 4,000 (in FIG. 2, m=30), CHISSO CORPORATION) was dissolved in 25 ml of water (solution A). A diglycidylether compound (EG-DGE; in Figure, n=1, 0.124 g; n=9, 0.375 g; n=23, 0.985 g) was dissolved in 750 μl of ethanol (solution B). The solutions A and B were mixed and reacted in an oil bath at 70° C. for 18 hours. Then, the solution was subjected to dialysis (Spectra/Por® 7, MWCO 10,000) such that low molecular weight compounds were removed. After the dialysis, the solution was concentrated by means of an evaporater to prepare an aqueous solution of high-molecular-weight ε-PLL. A portion of the solution was lyophilized in order to calculate the weight concentration. The solution was then subjected to elemental analysis in order to confirm the purity and the amine content (Table 2).

TABLE 2

High-molecular-weight ε-PLL

| Compound | Production amount (mg) | Yield (%) | Elemental analysis (%) C | H | N |
|---|---|---|---|---|---|
| 1EG-PLL | 147 | 38 | 49.80 | 8.95 | 15.19 |
| 9EG-PLL | 426 | 41 | 51.95 | 8.91 | 11.57 |
| 23EG-PLL | 392 | 35 | 51.70 | 9.24 | 7.40 |

SDS-PAGE for Determining Molecular Weight of the High-Molecular-Weight ε-PLL

Figure 5:
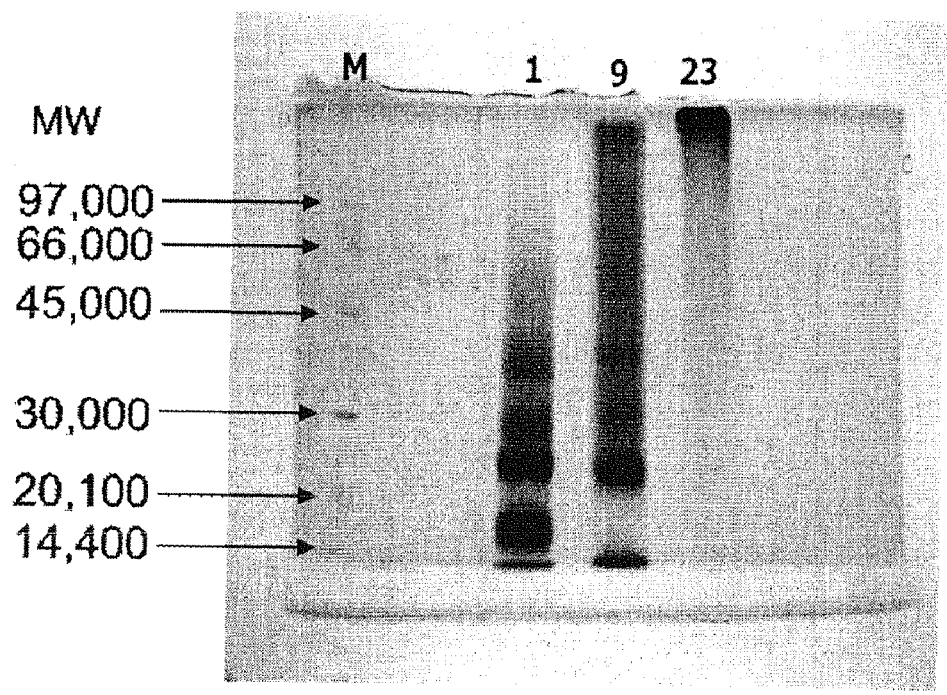
FIG. 5 is a photograph showing the result of SDS-PAGE of high-molecular-weight ε-PLL.

A separation gel whose acrylamide concentration was 15 w/v % was used for electrophoresis. A sample solution was obtained by adding 2 μl of ultrapure water (milliQ) and 5 μl of 2× sample buffer (0.125 M(mol/l) TRIS-buffer containing 10 w/v % 2-mercaptoethanol, 4 w/v % SDS and 10 w/v % sucrose) to 3 μl (1 mg/ml) of a sample to be tested. The sample was boiled at 95° C. for 3 minutes. Electrophoresis was conducted at 100V, 30 mA for about 2 hours and the resulting gel was stained with Coomassie Brilliant Blue solution overnight. Then, the gel was destained for about 12 hours and was photographed (FIG. 5). In FIG. 5, lane M shows the molecular weight marker, lane 1 shows 1EG-PLL (10 μg), lane 9 shows 9EG-PLL (10 μg), and lane 23 shows 23EG-PLL (10 μg). In all samples, high molecular-weight product bands which show the molecular weight greater than or equal to 10,000 could be confirmed.

Study of the Behavior of Hydrogel Formation

Figure 6:
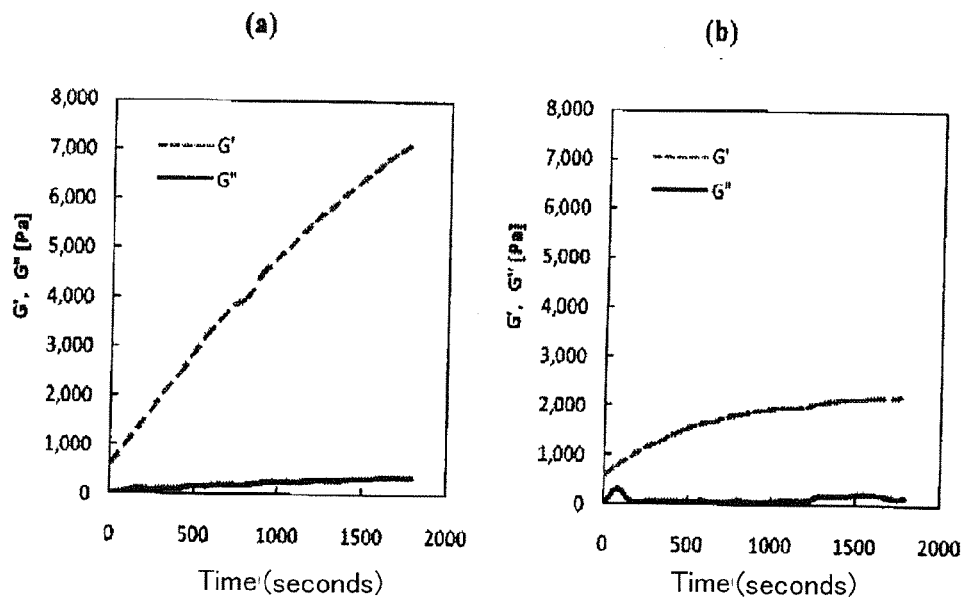
FIG. 6 shows graphs of the gelation behaviors of (a) hydrogel comprising 2.0-CHO and 1EG-PLL and (b) a commercially available hemostatic agent, fibrin adhesive.

Gel formation properties of the polyaldehyde aqueous solution and the high-molecular-weight ε-PLL were evaluated by adding dropwise the solutions to the sample table of a Rheometer (REOLOGICA Instruments AB, ViscoAnalyser VAR100, disc-diameter: 20 mm) simultaneously (the measurement temperature was 37° C.). The gelation time was determined as a time when the storage elastic modulus (G') becomes more than the loss elastic modulus (G") (G'>G") and the gel strength was determined as an absolute value of G'. As a representative result, the gel formulation property that was exhibited by mixing 2.0-CHO as a polyaldehyde and 1EG-PLL as a high-molecular-weight ε-PLL at a ratio of —CHO/—NH₂ of 0.27 is shown in FIG. 6-a.

It was found that the mixture comprising 2.0-CHO and 1EG-PLL turned into a gel within 1 second. As a comparative example, the gel-forming property of a hydrogel formed according to the formulation of Bolheal (KAKETSUKEN—The chemo-Sero-Therapeutic Research Institute), which is one commercially available hemostatic agent (fibrin adhesive), is shown in FIG. 6-b. The gel strength of the hydrogel comprising 2.0-CHO and 1EG-PLL was found to be superior to that of the fibrin adhesive.

Figure 7:
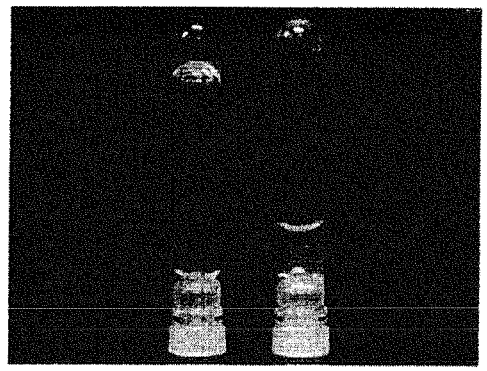
FIG. 7 shows the appearance of the hydrogel comprising 2.0-CHO and 1EG-PLL.

In addition, the appearance of the hydrogel comprising 2.0-CHO and 1EG-PLL is shown in FIG. 7. In FIG. 7, the left side is a state of the gel comprising 2.0-CHO and 1EG-PLL observed ten minutes after mixing and the right side is a state of a mixture comprising β-1,3-glucan (0-CHO-β-1,3-glucan) without aldehyde groups which had not been subjected to the periodate oxidation and 1EG-PLL observed ten minutes after mixing. It was found that the formation of the Schiff bases between aldehyde groups and amine groups was required for the formation of a hydrogel.

Figure 8:
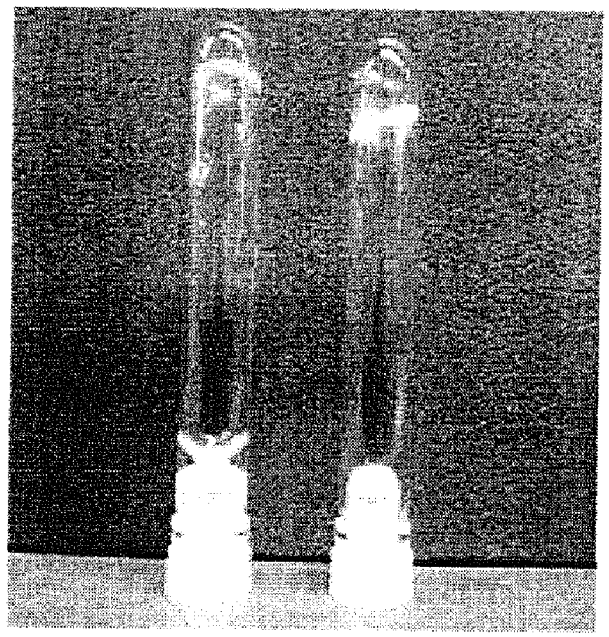
FIG. 8 shows the appearance of the hydrogel comprising 10-CHO or Alkali-10-CHO and 23EG-PLL.

Further, effects of periodate oxidation conditions (neutral or alkaline conditions) of β-1,3-glucan on the hydrogel formation of polyaldehyde were examined. The appearance of the hydrogel is shown in FIG. 8. FIG. 8(a) shows a state of a mixture comprising 10-CHO and 23EG-PLL observed ten minutes after mixing and FIG. 8(b) shows a state of a mixture comprising Alkali-10-CHO and 23EG-PLL observed ten minutes after mixing. The gel comprising Alkali-10-CHO which was prepared under alkaline conditions had more water content than that comprising the polyaldehyde prepared under neutral conditions. In fact, when the swelling ratio was calculated, the swelling ratio of a gel comprising 10-CHO or Alkali-10-CHO was 180% or 580%, respectively. It was found that the hydrogel comprising Alkali-10-CHO which was prepared under alkaline conditions was superior to those comprising polyaldehyde prepared under neutral conditions.

Figure 9:
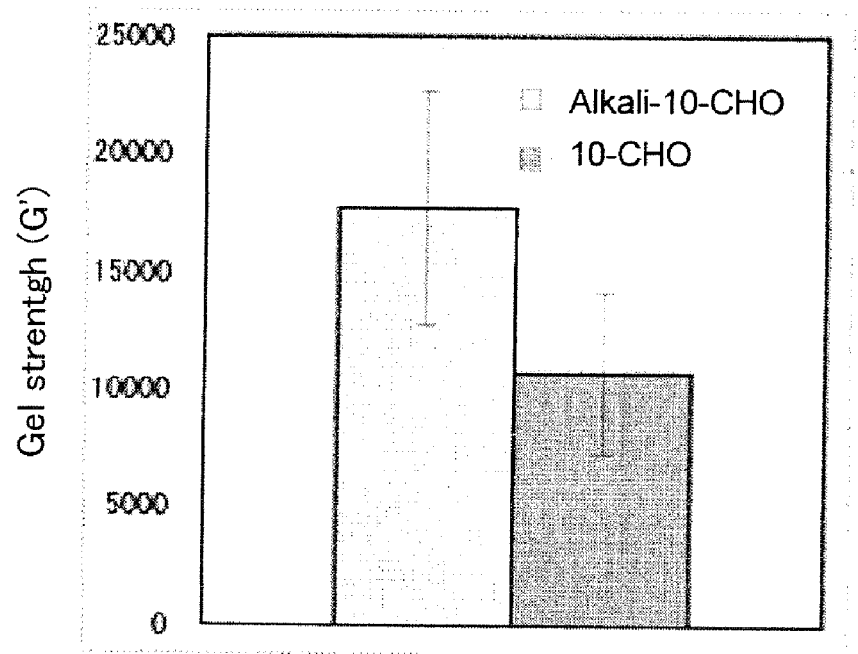
FIG. 9 consists of graphs showing the gelation behaviors of hydrogel comprising 10-CHO and 23EG-PLL and hydrogel comprising Alkali-10-CHO and 23EG-PLL.

Then, the gel formation behavior of a gel comprising 10-CHO or Alkali-10-CHO was observed by using a Rheometer. The result is shown in FIG. 9. Though there was no statistically significant difference (p=0.054, N=3), the gel strength of the hydrogel comprising polyaldehyde which had been aldehydated under alkaline conditions was better than that of the hydrogel comprising 10-CHO synthesized under neutral conditions.

Study of Hemostatic Effects Observed by Using Rats

Extra-large rats whose age in months was unknown were used for determining hemostatic effects. Rats were anesthetized by intraperitoneal anesthesia using 0.5 ml Nembutal stock solution and inhalation anesthesia using halothane. The inhalation anesthesia was continued during surgical procedures. The hemostatic models employed include three models, i.e., I. the small hemorrhage model by small vessel incision in abdominal wall muscle layers, II. the venous large hemorrhage model by centesis of inferior vena cava, and III. the arterial large hemorrhage model by femoral artery incision.

Hemostatic Procedures and Evaluation Procedures of Tissue Adhesion by Using Rats The hemostatic procedures were conducted using the following types of materials: (1) hydrogel (10-CHO+9EG-PLL)+collagen InStat (InStat means hereinafter InStat®; collagen sheet hemostatic agent (Johnson & Johnson K.K.)), (2) hydrogel (Alkali-10-CHO+23EG-PLL)+collagen InStat, (3) Bolheal (Bolheal®; living tissue adhesive (KAKETSUKEN))+collagen InStat (a positive control) and (4) only collagen InStat (a negative control). The concentrations of aqueous solutions of each compound used for the hemostatic procedures are shown in Table 3.

TABLE 3

Weight concentrations of each compound used for the hemostatic procedures

| Compound | mg/ml |
| --- | --- |
| 10-CHO | 30.0 |
| Alkali-10-CHO | 35.6 |
| 9EG-PLL | 341 |
| 23EG-PLL | 391 |

In the hemostatic procedures using the materials (1) and (2), the aldehyde derivative was infiltrated into collagen InStat and InStat was applied to the hemorrhagic spot. To the InStat, one or two drops of nEG-PLL were added and the hemorrhagic spot was lightly pressed with tweezers for 10-20 seconds. After the hemorrhage of the affected area was confirmed as having been arrested, InStat was removed by a cotton swab and the adhesiveness of InStat to tissues was observed. In the hemostatic procedure using material (3), fibrinogen was infiltrated into collagen InStat and InStat was applied to the hemorrhagic spot. To the InStat, one or two drops of thrombin solution were added and the hemorrhagic spot was lightly pressed with tweezers for 10-20 seconds. After the hemorrhage of the affected area was confirmed as having been arrested, InStat was removed by means of a cotton swab and the adhesiveness of InStat to tissues was observed. In the hemostatic procedure using material (4), InStat was applied to the hemorrhagic spot and the hemorrhagic spot was lightly pressed with tweezers for 10-20 seconds. After the hemorrhage of the affected area was confirmed as having been arrested, InStat was removed by means of a cotton swab and the adhesiveness of InStat to tissues was observed.

Methods for Preparing a Small Hemorrhage Model of Small Vessels of Abdominal Wall Muscle Layers and the Results of the Hemostasis In the small hemorrhage model of small vessels of abdominal wall muscle layers, rats were placed supine and the epidermis was removed by the median incision of the abdomen with a microsurgery device in order to expose the small vessels. The exposed abdominal wall muscle layers were subjected to a sharp incision such that bleeding occurred. Then, the hemostatic effects of the above materials (1) to (3) were determined. In order to prepare a venous large hemorrhage model by centesis of inferior vena cava, the abdomen was opened to around the breastbone by a surgical device and fat or the like was removed, if necessary. The exposed inferior vena cava was subjected to centesis by means of a syringe needle such that bleeding occurred. Then, the hemostatic effects of the above materials (1) to (4) were determined. In order to prepare an arterial large hemorrhage model by femoral artery incision, the abdomen of a rat was opened and the femoral artery on the left-foot side was exposed. The femoral artery was subjected to a sharp incision such that bleeding occurred. Then, the hemostatic effects of the above materials (1) and (2) were determined.

Regarding the hemostasis of the small hemorrhage model, the hemorrhages of the abdominal wall muscle layers caused by the small vessel incision were confirmed as being completely arrested by all (1) to (3) materials.

Methods for Preparing a Small Hemorrhage Model of Small Vessels of Abdominal Wall Muscle Layers In the small hemorrhage model of small vessels of abdominal wall muscle layers, rats were placed supine and the epidermis was removed by median incision of the abdomen with a microsurgery device such that small vessels were exposed.

The exposed abdominal wall muscle layers were subjected to a sharp incision such that bleeding occurred. The hemostatic effects of the above materials (1) to (3) were determined.

Methods for Preparing an Arterial Large Hemorrhage Model by Femoral Artery Incision In order to prepare an arterial large hemorrhage model by the femoral artery incision, the abdomen of a rat was opened and the femoral artery on the left foot side was exposed and was subjected to sharp incision such that bleeding occurred. The hemostatic effects of the above materials (1) and (2) were determined.

The Hemostatic Effects Observed by Using Rat Hemorrhage Models

I. The small hemorrhage model with the small vessel incision of abdominal wall muscle layers II. The venous large hemorrhage model with centesis of inferior vena cava III. The arterial large hemorrhage model with the femoral artery incision The results of the above three hemostatic experiments are shown in Table 4. The hydrogel obtained by using the polyaldehyde synthesized under alkaline conditions was found to exhibit the hemostatic effect which was comparable to a commercially available hemostatic agent, Bolheal.

TABLE 4

Results of the measurement of hemostatic effects

|     | I       | II  | III     |
|-----|---------|-----|---------|
| (1) | +       | +   | −       |
| (2) | ++      | ++  | −       |
| (3) | ++      | ++  | NO DATA |
| (4) | NO DATA | −   | NO DATA |

Studies of Tissue-Adhesive Effects on Tissues by Using Rats (1) Hydrogel (10-CHO+95G-PLL)+collagen InStat (2) Hydrogel (Alkali-10-CHO+235G-PLL)+collagen InStat (3) Bolheal+collagen InStat (a positive control)

Using the above hemostatic materials (1) to (3), effects of tissue adhesives on damaged areas and normal tissues were evaluated. The areas to be evaluated were: i. each damaged area, ii. muscle, iii. cardiac muscle, iv. liver, v. bowel, vi. peritoneum and vii. paper. The effects of tissue adhesives were evaluated as follows. An aldehyde derivative or fibrinogen was infiltrated into collagen InStat and the InStat was applied to the area to be evaluated. A solution of nEG-PLL or thrombin was dropped into InStat. The InStat was lightly pressed for 10-20 seconds by means of tweezers, and the InStat was removed by a cotton swab and was subjected to the observation of the adhesiveness to tissues. The results obtained by using the above three types of tissue adhesive materials are shown in Table 5. Regarding the adhesiveness on the above I to vii, when the material (1) was used, hardly any tissues other than vii exhibited the adhesion. When material (2) was used, though the material did not adhere to tissues with smooth surfaces such as v and vi, the material adhered to tissues other than v and vi. However, the adhesion strength was weak (about 0.5 fold of (3)). When material (3) was used, the material adhered to tissues other than v with significant strength.

TABLE 5

Evaluation of tissue adhesives

|     | i  | ii | iii     | iv | V       | vi      | vii |
|-----|----|----|---------|----|---------|---------|-----|
| (1) | −  | −  | −       | −  | −       | −       | +   |
| (2) | +  | +  | NO DATA | −  | −       | +       | +   |
| (3) | ++ | ++ | +       | −  | NO DATA | NO DATA | ++  |

* Regarding i, bleeding areas other than those with arterial bleedings were evaluated.

INDUSTRIAL APPLICABILITY

The tissue adhesive hydrogel of the present invention which is obtained by using the combination product comprising the polyaldehyde (1) and the polyamine (2) can be used as a hemostatic agent for brain, heart, liver and the like, a vascular blockage agent, a lung-sealant or a sealant for aneurysm. Further, the tissue-adhesive hydrogel of the present invention can be used as an adhesive for living tissues which can stick a soft tissue to another soft tissue such as anastomotic sites of blood vessels, a soft tissue to a hard tissue such as a living tendon and a bone or a parodontal tissue and a tooth, or a hard tissue to another hard tissue such as a bone and a bone or a tooth and a tooth.

The invention claimed is:

1. A combination product comprising:
   (1) a polyaldehyde obtained by introducing an aldehyde group into a branched glucose in a β-1,3-glucan by means of the periodate oxidation of said branched glucose under alkaline conditions, wherein the ratio of said branched glucose in β-1,3-glucan is equal to or greater than 60%, and
   (2) a polyamine obtained by cross-linking ε-poly-L-lysine with a cross-linking agent,
   wherein the ratio of said branched glucose in β-1,3-glucan means the proportion of the number of branched glucoses relative to the number of main chain glucoses.

2. The combination product according to claim 1, wherein said polyaldehyde and/or said polyamine is in the form of an aqueous solution.

3. The combination product according to claim 1, wherein said cross-linking agent is diglycidylether.

4. The combination product according to claim 1, wherein the molecular weight of said polyamine as determined by SDS-PAGE is equal to or greater than 10,000.

5. A tissue adhesive hydrogel produced by using the combination product according to claim 1.

6. A method for producing the tissue adhesive hydrogel according to claim 5, which comprises mixing:
   (1) a polyaldehyde obtained by introducing an aldehyde group into a branched glucose in a β-1,3-glucan by means of the periodate oxidation of said branched glucose under alkaline conditions, wherein the ratio of said branched glucose in β-1,3-glucan is equal to or greater than 60%, and
   (2) a polyamine obtained by cross-linking ε-poly-L-lysine with a cross-linking agent.

7. A hemostatic composition comprising a hydrogel obtained by mixing:
   (1) a polyaldehyde obtained by introducing an aldehyde group into a branched glucose in a β-1,3-glucan by means of the periodate oxidation of said branched glucose under alkaline conditions, wherein the ratio of said branched glucose in β-1,3-glucan is equal to or greater than 60%, and (2) a polyamine obtained by cross-linking ε-poly-L-lysine with a cross-linking agent.

8. A hemostatic composition comprising:
(1) a polyaldehyde obtained by introducing an aldehyde group into a branched glucose in a β-1,3-glucan by means of the periodate oxidation of said branched glucose under alkaline conditions, wherein the ratio of said branched glucose in β-1,3-glucan is equal to or greater than 60%,
(2) a polyamine obtained by cross-linking ε-poly-L-lysine with a cross-linking agent, and
(3) a hemostatic sponge or sheet.

9. The hemostatic composition according to claim 8, wherein said hemostatic sponge or sheet is a collagen sponge.

10. An adhesive for living tissue comprising a hydrogel obtained by mixing:
(1) a polyaldehyde obtained by introducing an aldehyde group into a branched glucose in a β-1,3-glucan by means of the periodate oxidation of said branched glucose under alkaline conditions, wherein the ratio of said branched glucose in β-1,3-glucan is equal to or greater than 60%, and
(2) a polyamine obtained by cross-linking ε-poly-L-lysine with a cross-linking agent.

11. The combination product according to claim 1, wherein the molecular weight of said polyamine obtained by cross-linking ε-poly-L-lysine with a cross-linking agent is from 4,000 to 200,000.

* * * * *